(12) United States Patent
Saunders (10) Patent No.: US 7,189,214 B1
(45) Date of Patent: Mar. 13, 2007

(54) MULTI-AXIS CERVICAL AND LUMBAR TRACTION TABLE

(75) Inventor: H. Duane Saunders, Eden Prairie, MN (US)

(73) Assignee: The Saunders Group, Inc., Chaska, MN (US)

( * ) Notice: Subject to any disclaimer, the term of this patent is extended or adjusted under 35 U.S.C. 154(b) by 716 days.

(21) Appl. No.: 10/054,631

(22) Filed: Jan. 22, 2002

(51) Int. Cl.
*A61F 5/00* (2006.01)

(52) U.S. Cl. .............................. 602/32; 5/618; 606/243

(58) Field of Classification Search ............ 602/32–40; 128/72, 71, 84 R, 76 R, 78
See application file for complete search history.

(56) References Cited

U.S. PATENT DOCUMENTS

| | | |
|---|---|---|
| 738,283 A | 9/1903 | Blomqvist |
| 1,205,649 A | 11/1916 | Miller |
| 1,242,688 A | 10/1917 | Hawley |
| 1,301,276 A | 4/1919 | Kroetz |
| 1,803,556 A | 5/1931 | Nugent |
| 1,984,520 A | 12/1934 | Curtis |
| 2,166,229 A | 7/1939 | Anderson |
| 2,273,088 A | 2/1942 | Byers |
| 2,534,587 A | 12/1950 | Fisher et al. |
| 2,554,337 A | 5/1951 | Lampert |
| 2,689,127 A | 9/1954 | Silverton et al. |
| 2,723,663 A | 11/1955 | Davis |
| 2,733,712 A | 2/1956 | Wuesthoff |
| 2,831,482 A | 4/1958 | Cobb |
| 2,910,061 A | 10/1959 | Rabjohn |
| 2,966,906 A | 1/1961 | Wiltrout |
| 3,060,925 A | 10/1962 | Honsaker et al. |
| 3,176,684 A | 4/1965 | Walsh |
| 3,293,667 A | 12/1966 | Ohrberg |
| 3,336,922 A | 8/1967 | Taylor |
| 3,387,605 A | 6/1968 | Schmidt |
| 3,413,971 A | 12/1968 | Evans |
| 3,522,802 A | 8/1970 | Morton |
| 3,548,817 A | 12/1970 | Mittasch |
| 3,554,189 A | 1/1971 | Hendrickson |
| 3,561,434 A | 2/1971 | Kilbey |
| 3,596,655 A | 8/1971 | Corcoran |
| 3,621,839 A | 11/1971 | Barthe |
| 3,675,646 A | 7/1972 | Corcoran |
| 3,827,429 A | 8/1974 | Heikes |
| 3,828,377 A | 8/1974 | Fary, Sr. |
| 3,847,146 A | 11/1974 | Cushman |
| 3,888,243 A | 6/1975 | Powlan |
| 3,937,216 A | 2/1976 | Brown |

(Continued)

FOREIGN PATENT DOCUMENTS

FR 997 691 1/1952

*Primary Examiner*—Henry Bennett
*Assistant Examiner*—Shumaya B. Ali
(74) *Attorney, Agent, or Firm*—Faegre & Benson LLP (57) ABSTRACT

A multi-axis cervical and lumbar traction table and method of using same. The traction table includes a support frame with a first body supporting portion and a second body supporting portion. The first body supporting portion is moveable relative to the second body supporting portion along a longitudinal axis. A securing system adapted to secure a patient to the first and second body supporting portions is provided. Linking mechanism is adapted to move the first body supporting portion along a path relative to the second body supporting portion, wherein the path comprises at least one rotational degree of freedom.

58 Claims, 7 Drawing Sheets

U.S. PATENT DOCUMENTS

| | | | |
|---|---|---|---|
| 3,957,040 A | 5/1976 | Calabrese | |
| 4,146,021 A | 3/1979 | Brosseau et al. | |
| 4,154,478 A | 5/1979 | Cohune | |
| 4,166,459 A | 9/1979 | Nightingale | |
| 4,242,946 A | 1/1981 | Toliusis | |
| 4,320,749 A | 3/1982 | Highley | |
| 4,356,816 A | 11/1982 | Granberg | |
| 4,378,791 A * | 4/1983 | Sarrell | 602/32 |
| 4,428,276 A | 1/1984 | Loveless | |
| 4,436,303 A | 3/1984 | McKillip et al. | |
| 4,466,427 A | 8/1984 | Granberg | |
| 4,545,572 A | 10/1985 | Day | |
| 4,577,730 A | 3/1986 | Porter | |
| 4,579,109 A | 4/1986 | Lundblad | |
| 4,583,532 A | 4/1986 | Jones | |
| 4,649,907 A | 3/1987 | Whitehead et al. | |
| 4,655,200 A * | 4/1987 | Knight | 606/245 |
| 4,664,101 A | 5/1987 | Granberg | |
| 4,669,455 A | 6/1987 | Bellati | |
| 4,722,328 A | 2/1988 | Scott et al. | |
| 4,736,736 A | 4/1988 | Moers et al. | |
| 4,760,842 A | 8/1988 | Holmes | |
| 4,771,493 A | 9/1988 | Park | |
| RE32,791 E | 11/1988 | Saunders | |
| 4,805,603 A | 2/1989 | Cumberland | |
| 4,832,007 A | 5/1989 | Davis, Jr. et al. | |
| 4,866,796 A | 9/1989 | Robinson | |
| 4,890,604 A | 1/1990 | Nelson | |
| 4,915,101 A | 4/1990 | Cuccia | |
| 4,944,054 A | 7/1990 | Bossert | |
| 4,951,654 A | 8/1990 | Gambale et al. | |
| 4,981,034 A | 1/1991 | Haeg | |
| 4,981,148 A | 1/1991 | Fuller | |
| 4,991,572 A | 2/1991 | Chases | |
| 4,995,378 A | 2/1991 | Dyer et al. | |
| 5,052,378 A | 10/1991 | Chitwood | |
| 5,067,483 A | 11/1991 | Freed | |
| 5,092,322 A | 3/1992 | Gantz | |
| 5,138,729 A * | 8/1992 | Ferrand | 5/713 |
| 5,154,186 A | 10/1992 | Laurin et al. | |
| 5,169,160 A | 12/1992 | Gaskill et al. | |
| 5,181,904 A | 1/1993 | Cook et al. | |
| 5,231,719 A * | 8/1993 | Schnelle | 5/614 |
| 5,265,625 A | 11/1993 | Bodman | |
| 5,279,010 A * | 1/1994 | Ferrand et al. | 5/600 |
| 5,299,334 A * | 4/1994 | Gonzalez | 5/607 |
| 5,306,231 A | 4/1994 | Cullum et al. | |
| 5,308,359 A * | 5/1994 | Lossing | 606/242 |
| 5,320,641 A * | 6/1994 | Riddle et al. | 606/243 |
| 5,345,629 A * | 9/1994 | Ferrand | 5/710 |
| 5,360,392 A | 11/1994 | McCoy | |
| 5,382,226 A | 1/1995 | Graham | |
| 5,441,479 A | 8/1995 | Chitwood | |
| 5,454,781 A | 10/1995 | Chitwood | |
| 5,474,086 A | 12/1995 | McCormick et al. | |
| 5,478,307 A * | 12/1995 | Wang | 602/32 |
| 5,505,691 A | 4/1996 | Fenkell | |
| 5,569,175 A | 10/1996 | Chitwood | |
| 5,578,060 A | 11/1996 | Pohl et al. | |
| 5,653,678 A | 8/1997 | Fulk | |
| 5,662,597 A | 9/1997 | Chitwood | |
| 5,709,649 A | 1/1998 | Chitwood | |
| 5,722,941 A | 3/1998 | Hart | |
| 5,868,471 A | 2/1999 | Graham et al. | |
| 5,922,011 A | 7/1999 | Cuccia | |
| 5,957,876 A | 9/1999 | D'Amico | |
| 6,007,568 A * | 12/1999 | Harrell et al. | 606/242 |
| 6,059,548 A | 5/2000 | Campbell et al. | |
| 6,108,838 A * | 8/2000 | Connolly et al. | 5/609 |
| 6,152,950 A | 11/2000 | Shealy et al. | |
| 6,171,273 B1 | 1/2001 | Saunders | |
| 6,277,141 B1 * | 8/2001 | Lake | 606/243 |
| 6,468,240 B1 * | 10/2002 | Saunders | 602/38 |
| 6,506,174 B1 * | 1/2003 | Saunders et al. | 602/33 |
| 6,547,809 B1 | 4/2003 | Cuccia | |
| 6,652,564 B1 * | 11/2003 | Harris et al. | 606/237 |
| 6,892,405 B1 | 5/2005 | Dimitriu et al. | |
| 6,905,508 B2 | 6/2005 | Cuccia | |

* cited by examiner

MULTI-AXIS CERVICAL AND LUMBAR TRACTION TABLE

FIELD OF THE INVENTION

The present invention relates to a therapeutic traction apparatus, and in particular, to a multi-axis traction device with a first body supporting portion moveable relative to a second body supporting portion and a method of using the therapeutic apparatus to apply traction to a patient.

BACKGROUND OF THE INVENTION

Back and neck pain are common conditions that can adversely affect both work and leisure activities. One commonly used non-surgical approach to alleviating back pain in patients is the application of traction forces. Traction tables are used to apply traction forces to the human body through the application of tension force along the spinal column. Traction tables are generally used to relieve pain in two areas, the lumbar region, which is located between a patient's ribs and hipbones, and the cervical region, which corresponds to the patient's neck region.

A traditional system for applying traction to a patient is through the use of weights and pulleys. The method entails placing a patient in the supine position and securing the patient to a resting surface. Cords are then extended from the patient, looped around suspended pulleys and tied to raised weights which are released to provide a gravitational force. The weights thereby apply traction to the patient's back. The system has had only limited success because it does not sufficiently isolate the region of the body to which the force is to be applied. Furthermore, the system does not adequately treat patients with painful postural deformities, for example a flexed, laterally shifted posture often seen in patients suffering from a herniated lumbar disc.

U.S. Pat. No. 4,890,604 (Nelson) discloses a traction assembly that applies traction under the inclined weight of the patient. The traction assembly includes a stationary stand supportable on a ground or floor surface and a table assembly connected to the stand. The table assembly includes a frame that is rotatably assembled to the stand for limited rotation about a horizontal axis. A flat platform or table is slidably assembled to the frame for back-and-forth movement under gravitational influence in a longitudinal direction perpendicular to the axis of rotation of the frame. Restraints are connected to the patient's ankles and head. Upon rotation of the frame on the stand to incline the platform, the body is put in traction according to the weight of the body and the degree of inclination.

One shortcoming of this invention is that the degree of applied force depends upon the weight of the body and the inclination of the frame, rather than by an independent force. Furthermore, the assembly does not compensate for a patient's postural deformities. For example, a patient with a herniated lumbar disc may not be able to lie perfectly straight on the table, reducing the effectiveness of the gravitational force. Further yet, because the patient is anchored to the table at the neck and ankles, the table does not sufficiently concentrate traction force on the specific area in need of treatment, for example the lumbar region of the body.

U.S. Pat. No. 4,995,378 (Dyer et al.) discloses a therapeutic table with a frame and a table top having an upper-body section rigid with respect to the frame, and a lower-body section slidable with respect to the frame. The sections provide a separable surface for a patient to lie prone face down. Hand grips rigid with respect to the upper-body section extend upwardly of the plane of the table top to be accessible by a patient with arms above head along a plane of the axis of the patient's spine to provide anchoring for the upper body. An anchor is connected to the lower-body section to which a pelvic belt can be connected. A cylinder and piston drive is provided to slide the lower-body section to cyclically increase and decrease the distance between the hand grips and the pelvic belt anchors.

Although the Dyer device avoids the use of weights and pulleys, it still requires a cumbersome harness to be placed around the patient that is anchored to the end of the lower-body section of the table. It also requires the patient to lie prone and hold on to hand grips to properly apply the force. The traction force is thus extended along the entirety of the patient's spine, rather than focusing on the lumbar region. Dyer does not disclose a multi-axis traction device that can compensate for patient postural deformities that hinder the application of traction forces along the spine.

BRIEF SUMMARY OF THE INVENTION

The present invention provides a multi-axis traction device that is capable of treating back pain for a patient with postural deformities that hinder the traditional application of longitudinal traction force along the spine. The present traction device isolates and concentrates traction force on specific areas of the body, for example the lumbar region, without applying the force along the entirety of the patient's body.

The present therapeutic apparatus comprises a support frame with first and second body supporting portions. The first body supporting portion is moveable relative to the second body supporting portion along a longitudinal axis. A securing system is adapted to secure a patient to the first and second body supporting portions. A linking mechanism provides the first body supporting portion movement along a path relative to the second body supporting portion, the path comprising at least one rotational degree of freedom.

In another embodiment, the securing system includes a first belt attachable to the first body supporting portion and a second belt attachable to the second body supporting portion, the belts being adapted to secure a patient to the first and second body supporting portions. The embodiment can further provide an actuator adapted to move the first body supporting portion relative to the second body supporting portion and one or more locking mechanisms adapted to releasably retain the first body supporting portion in a plurality of locations along the path relative to the second body supporting portion.

The present invention further provides a method of using the therapeutic traction apparatus generally described above to provide traction to a patient's lumbar region. The method includes supporting the patient on the first and second body supporting portions; securing the patient to the first and second body supporting portions with the securing system; moving the first body supporting portion along a path relative to the second body supporting portion, the path comprising at least one rotational degree of freedom; and moving the first body supporting portion relative to the second body supporting portion along a longitudinal axis to increase and decrease the distance between the first and second body supporting portions.

DETAILED DESCRIPTION OF THE INVENTION

The present invention provides a therapeutic apparatus for treating a patient suffering from back pain. The apparatus is adapted to exert a therapeutic traction force on a patient's spine to relieve pressures on structures that may be causing pain. The apparatus is further capable of producing the forces and positions required to cause decompression of the intervertebral discs, that is, unloading due to distraction and positioning. The apparatus provided by the present invention can be used to treat many conditions, including, but not limited to back pain, neck pain, herniated disc, protruding disc, degenerative disc disease, posterior facet syndrome and sciatica.

Figure 1:
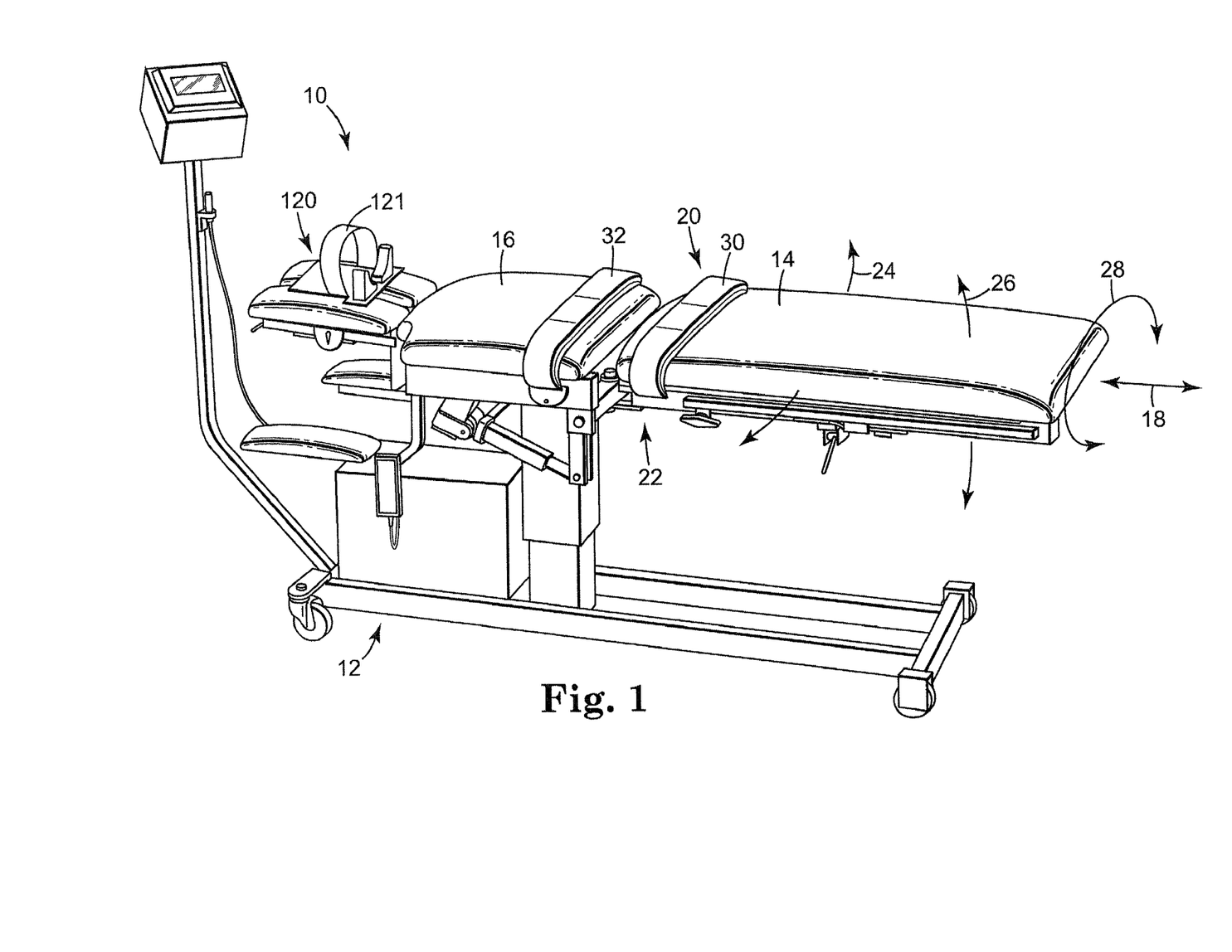
FIG. 1 illustrates a therapeutic apparatus in accordance with the present invention.

FIG. 1 illustrates a therapeutic apparatus 10 including a support frame 12 having a first body supporting portion 14 and a second body supporting portion 16. First body supporting portion 14 is capable of movement relative to second body supporting portion 16 along a longitudinal axis 18. As used herein, the term "longitudinal axis" refers to the axis along which a body supporting portion can be displaced. In FIG. 1, first body supporting portion 14 is adapted to generally support a patient's lower body while second body supporting portion 16 is adapted to support a patient's upper body. The present invention also contemplates the reverse (i.e. first body supporting portion supporting the patient's upper body and the second body supporting portion supporting the patient's lower body).

The therapeutic apparatus 10 further includes a securing system 20 adapted to secure a patient to the first and second body supporting portions 14, 16. Linking mechanism 22 is adapted to provide movement of the first body supporting portion 14 relative to second body supporting portion 16 along a path comprising at least one rotational degree of freedom. As used herein, "rotational degree of freedom" refers to rotational movement of a first body supporting portion relative to a second body supporting portion. Although the embodiment in FIG. 1 shows first body supporting portion 14 in a neutral position (i.e. along the same horizontal plane as the second body supporting portion 16), first body supporting portion is adapted to move along a path comprising up to three degrees of freedom, including but not limited to yaw movement along path 24, pitch movement along path 26, roll movement along path 28, or a combination thereof.

Securing system 20 is adapted to secure a patient to the first and second body supporting portions 14, 16. In the embodiment of FIG. 1, securing system 20 includes a first belt 30 attached to the support frame 12, and extending at least to each side edge of first body supporting portion 14, and a second belt 32 attached to the support frame 12 and extending at least to each side edge of second body supporting portion 16 in a similar manner. In FIG. 1, first and second belts 30, 32 comprise adjustable and releasable hook and loop fasteners, such as Velcro®. In another embodiment, the securing system 20 can be a Velcro® or other high friction surface on the body supporting surfaces 14, 16 with or without belts 30 and 32, pelvic and/or thoracic harnesses, pegs, binders or any combination of these devices.

Figure 2:
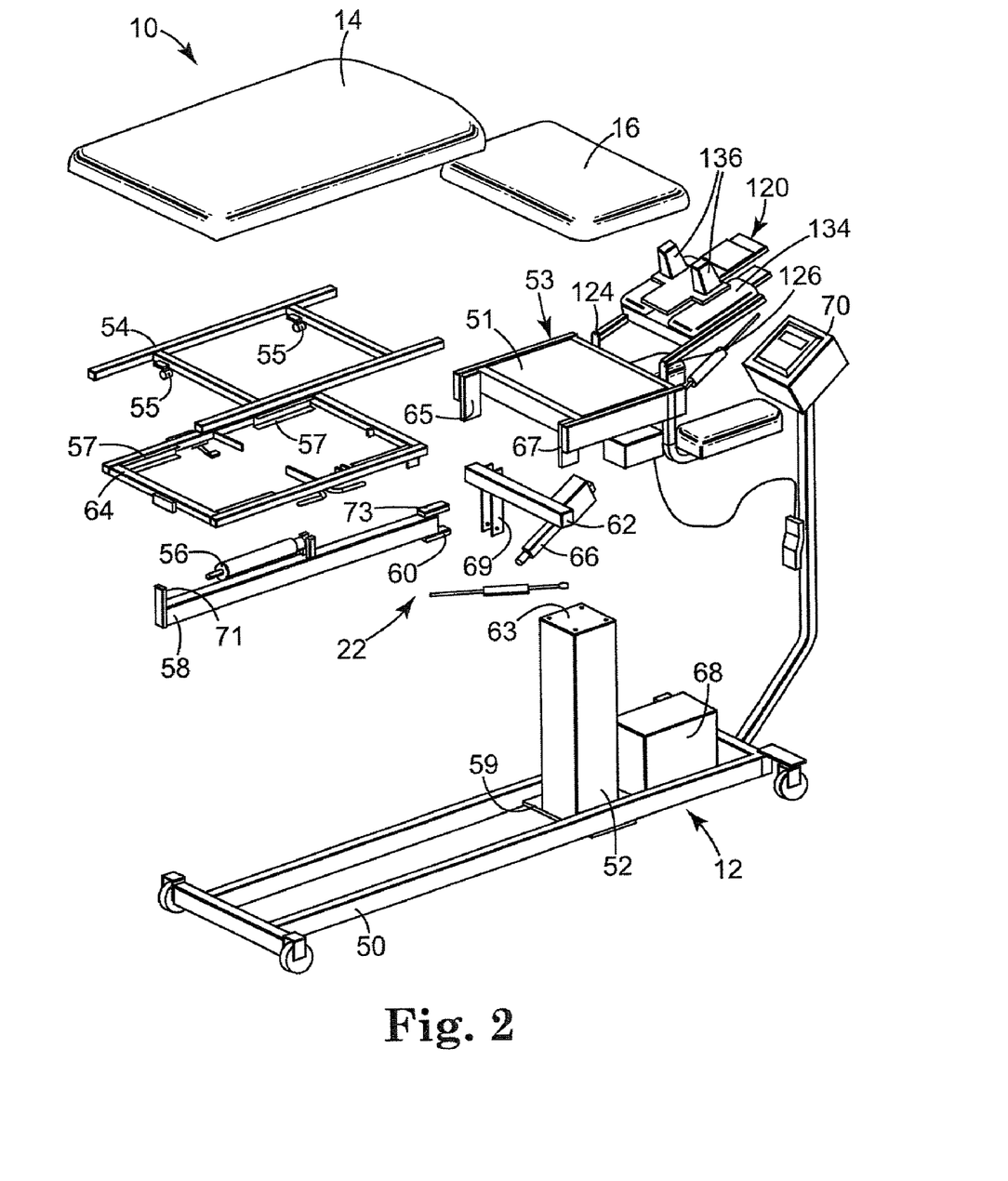
FIG. 2 illustrates an exploded view of the therapeutic apparatus of FIG. 1.

FIG. 2 illustrates an exploded view of the present therapeutic apparatus 10. Support frame 12 includes a base portion 50, a support member 52, and a platform portion 53. Base portion 50 supports the apparatus and is positioned on a generally horizontal surface. Support member 52 is secured to base member 50 at a lower portion 59, and to platform portion 53 at an upper portion 63. Support member 52 is thereby positioned in a vertical plane and is adapted to provide support for the first and second body supporting portions. Support member 52 also includes an actuator (not shown) for increasing or decreasing the height of the first and second body supporting portions relative to the base portion 50. Suitable actuators include pneumatic or hydraulic cylinders, linear motors, worm gears, rack and pinion systems, and the like. Preferably, support member 52 is capable of adjustment between about 25 inches to about 35 inches and is powered by a central source of compressed air 68.

In the illustrated embodiment, the second body supporting portion 16 is rigidly attached to a top side 51 of platform portion 53 and is positioned along a substantially horizontal plane. First body supporting portion 14 is pivotally secured to platform portion 53 by linking mechanism 22. As shown in FIG. 2, linking mechanism 22 comprises cantilever arm 58, yaw mechanism 60, pitch mechanism 62 and roll mechanism 64. Cantilever arm 58 is pivotally attached to pitch mechanism 62 by yaw mechanism 60 at pivot point 61 (See FIG. 6). Pitch mechanism 62 is pivotally attached to platform portion 53 at pivot points 65 and 67. Roll mechanism 64 is pivotally attached to cantilever arm 58 at pivot points 71 and 73. An actuator 66 can be secured to pitch mechanism 62 at lever 69, the actuator being adapted to facilitate movement along a path comprising at least one rotational degree of freedom, preferably facilitating at least pitch movement along path 26. Almost any type of actuator can be used, however, an actuator of the present invention is preferably powered by a single central source of compressed air 68.

Sliding mechanism 54 is slidably attached to roll mechanism 64. In the illustrated embodiment, sliding mechanism 54 includes rollers 55 that slide in tracks 57 on roll mechanism 64, although a variety of structures could be used. First body supporting portion 14 is secured to sliding mechanism 54 and is thereby capable of movement along longitudinal axis 18, as shown in FIG. 1. Preferably, first body supporting portion 14 is capable moving up to 6 inches along longitudinal axis 18. Actuator 56 can be secured to sliding mechanism 54 to facilitate movement of the first body supporting portion along longitudinal axis 18. Any type of suitable actuator can be used, including a pneumatic actuator, hydraulic actuator, rack and pinion structures, linear motors, worm gear, solenoids, and the like. In the illustrated embodiment, actuator 56 is a double acting piston powered by a central source of compressed air 68 and is capable of moving first body supporting portion 14 along longitudinal axis 18 with a force of up to about 200 pounds.

The present therapeutic apparatus 10 permits the actuator 56 to apply or remove a traction force to the patient without interfering with the operation of the yaw mechanism 60, pitch mechanism 62 or roll mechanism 64. In particular, any one or all of the yaw mechanism 60, pitch mechanism 62 and roll mechanism 64 can be adjusted before, during or after a traction force is applied to a patient. The therapeutic apparatus 10 has the added advantage that there are no rope and pulleys to interfere with the operation of the yaw mechanism 60, pitch mechanism 62 and/or roll mechanism 64 during traction.

Processor 70 receives input data, processes that data and communicates with a central source of compressed air 68 in response. In the illustrated embodiment, the processor has a digital display, incorporating touch screen capabilities. Processor 70 is adapted to receive, process and communicate to the traction apparatus almost any relevant treatment data, including the type of force (e.g. static or intermittent), force ramp up and ramp down times, force hold and rest times, magnitude of hold and rest forces, and treatment times. Optionally, the processor 70 is adapted to automatically adjusting the table height and/or pitch movement of the apparatus, as well as a patient control switch adapted to terminate treatment. As used herein, "processor" refers to any of a variety of general purpose or special purpose programmable computing devices, such as for example a PC or a programmable logic controller. In one embodiment, the processor 70 is a separate stand-alone computer, such as a PC.

The processor 70 can also store and retrieve pre-programmed traction protocols. For example, the therapist may develop a protocol for a particular patient that can be applied multiple time over the course of treatment. This protocol can be stored in the processor 70 for future use. A protocol can include any of the treatment variable available in the processor 70, including without limitation the type of force (e.g. static or intermittent), force ramp up and ramp down times, force hold and rest times, magnitude of hold and rest forces, and treatment times. The processor 70 also preferably assigns an index number or title to each protocol so that they can be easily retrieved. In another embodiment, the therapist generates a treatment protocol off-line on a separate computer system, such as a PC. The protocol is then uploaded to the processor 70 using conventional computer communication protocols and techniques, such as an RS-232 connection. This embodiment permits the treatment protocol to be sent electronically to other clinics at which the patient can receive treatment. One method of electronically transmitting a treatment protocol is using electronic mail over the Internet.

Figure 4:
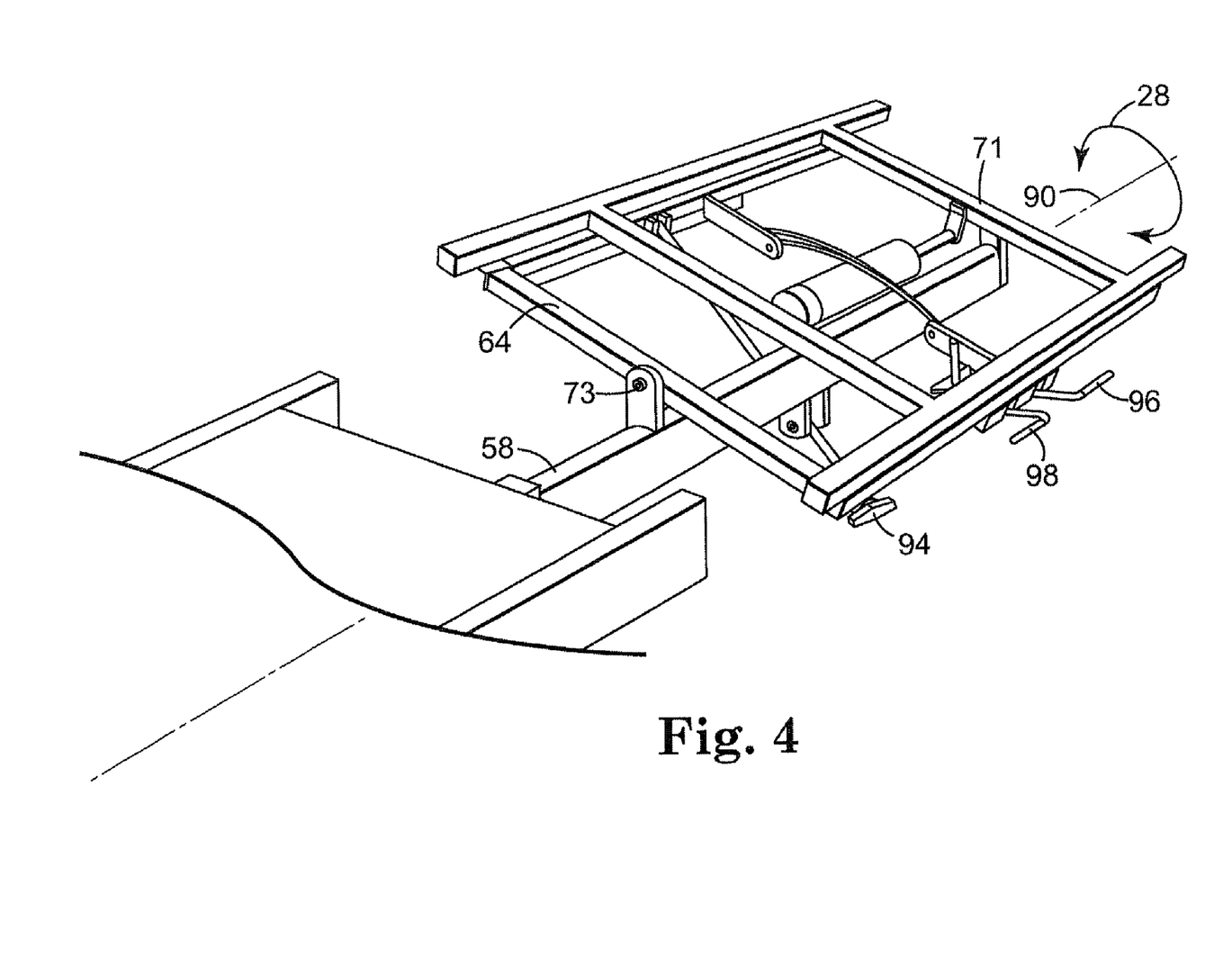
FIG. 4 is a cut-away perspective view of the therapeutic apparatus of FIG. 1.
Figure 5:
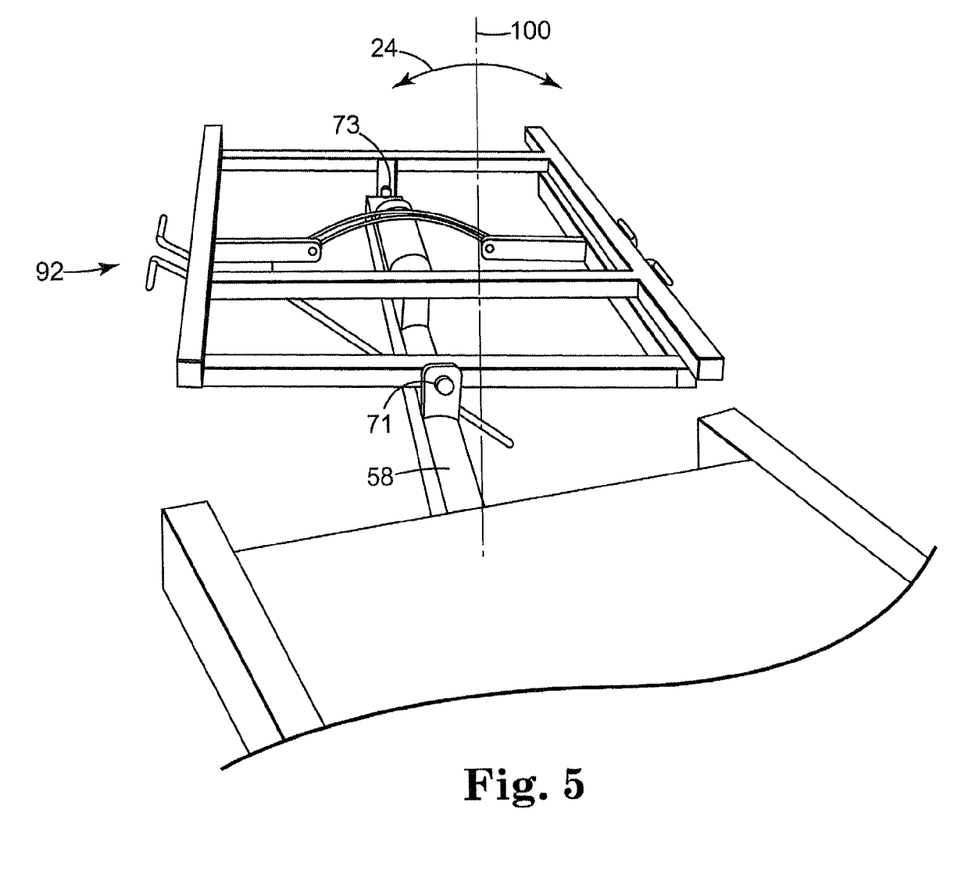
FIG. 5 illustrates an alternate cut-away view of the therapeutic traction table of FIG. 1.
Figure 6:
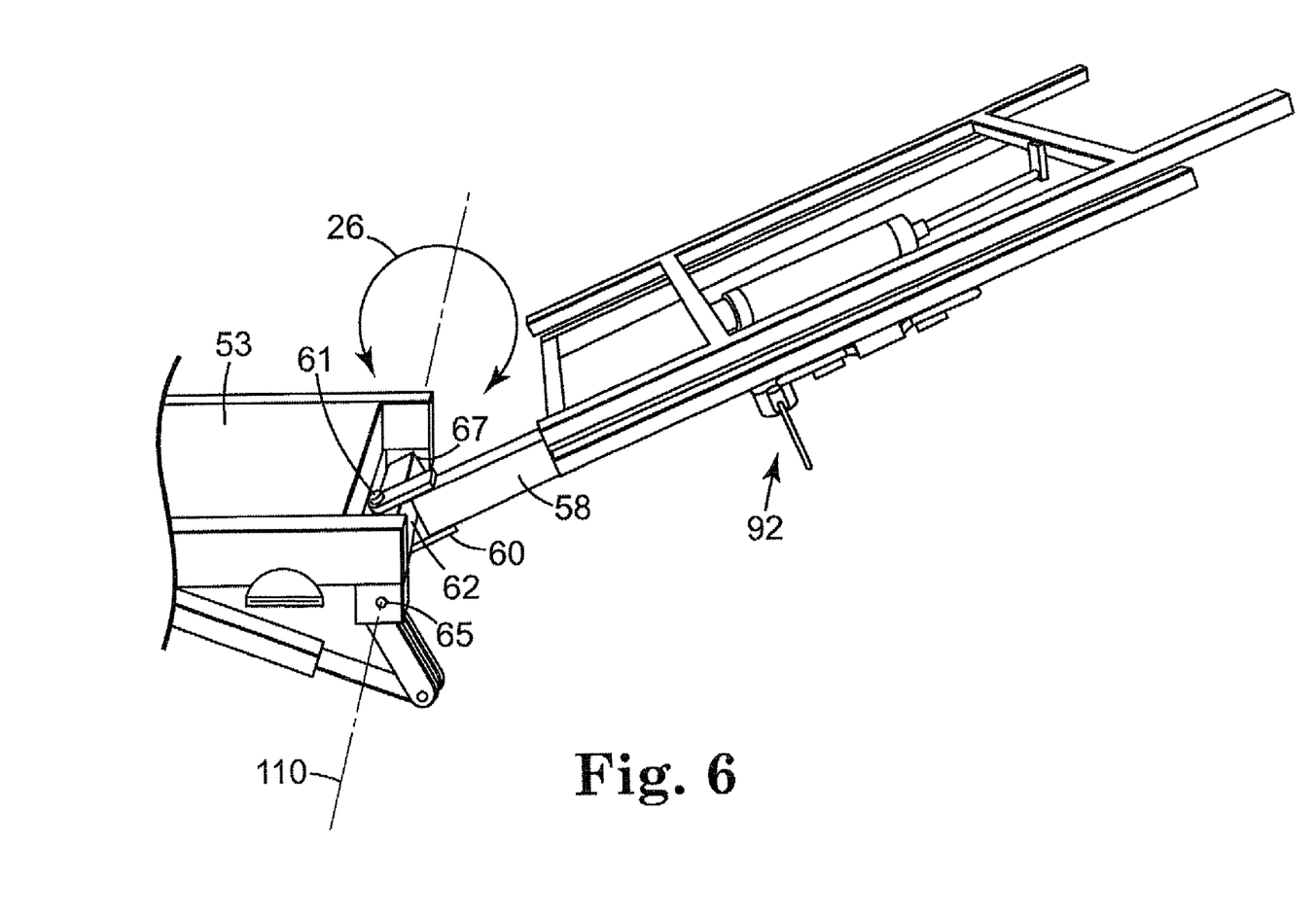
FIG. 6 illustrates another cut-away perspective view of the therapeutic apparatus of FIG. 1.

FIGS. 4, 5 and 6 show views of a portion of the present invention and illustrate examples of different rotational degrees of freedom of which first body supporting portion 14 is adapted to move relative to second body supporting portion 16. For example, in FIG. 4, roll mechanism 64 is pivotally secured to cantilever arm 58 at pivot points 71 and 73 to provide roll movement along path 28 about axis 90. It is preferable that roll mechanism 64 be capable of providing first body supporting portion 14 with up to about 15 degrees of rotation from the neutral position in either a clockwise or counterclockwise direction.

In FIG. 5, yaw mechanism 60 (see FIG. 6) is pivotally attached to pitch mechanism 62 at pivot point 61 (See FIG. 6) and is adapted to rotate cantilever arm 58 about axis 100 to provide yaw movement of the first body supporting portion 14 along path 24. Preferably, yaw mechanism 60 is capable of providing the first body supporting portion 14 up to about 15 degrees of rotation in either direction from the neutral position.

In FIG. 6, pitch mechanism 62 is secured to platform portion 53 at pivot points 65 and 67 and is adapted to rotate cantilever arm 58 about axis 110 to provide pitch movement along path 26, as shown in FIG. 1. Although FIG. 6 illustrates rotation flexed above the neutral position, embodiments of the present invention can also extend below neutral. Preferred embodiments of the present invention are capable of flexing up to about 25 degrees and extending down to about 20 degrees from the neutral position.

Although FIGS. 4, 5 and 6 each illustrate movement along a path defined by one rotational degree of freedom (e.g., pitch, roll or yaw), the present therapeutic apparatus 10 is capable of movement along paths that comprise two or more rotational degrees of freedom. That is, each of the rotational degrees of freedom are preferably independently and simultaneously adjustable. In a preferred embodiment, the first body supporting structure is capable of simultaneous movement along a path having three rotational degrees of freedom, comprising roll, yaw and pitch movement.

In the illustrated embodiment, the longitudinal axis 18 comprises the axis of movement of the sliding mechanism 54 relative to the cantilever arm 58. This movement along the longitudinal axis 18 is independent of the three degrees of freedom. The path upon which first body supporting portion 14 is positioned affects the direction and angle of its movement relative to second body supporting portion 16 along longitudinal axis 18. For example, if first body supporting portion 14 is positioned along path 26, 10 degrees above the neutral position, then longitudinal axis 18 will be located 10 degrees above the location of longitudinal axis 18 in FIG. 1.

The present invention provides at least one locking mechanism for releasably retaining first body supporting portion 14 along the path comprising at least one rotational degree of freedom. The apparatus may further provide a locking mechanism for releasably retaining the first body supporting portion 14 from movement along longitudinal axis 18. For example, FIG. 4 illustrates a first locking mechanism 94 adapted to releasably retain first body supporting portion 14 from longitudinal movement. Second locking mechanism 96 is adapted to releasably retain first body supporting portion 14 from yaw movement along path 24 and third locking member 98 is adapted to releasably retain first body supporting portion 14 from roll movement along path 28. In another embodiment, at least one locking mechanism is provided for each rotational degree of freedom. In one embodiment, the locking mechanisms 94, 96, 98 are an infinitely positionable mechanical lock, such as disclosed in U.S. Pat. No. 4,577,730 (Porter), or the linear positioning devices sold under the trade name Mecklok® from P. L. Porter Company of Woodland Hills, Calif.

The locking mechanisms 94, 96, 98 are preferably biased to a locked position. The locked position is released using the handles indicated by the reference numerals. The operator manually releases one or more of the locking mechanisms 94, 96, 98 and positions the first body supporting portion 14 in the desired configuration. Releasing the handle re-engages the locking mechanism 94, 96, 98. Positioning the first body supporting portion 14 along any combination of the three rotational degrees of freedom does not interfere with the movement of the sliding mechanism 54 along the longitudinal axis 18.

Figure 7:
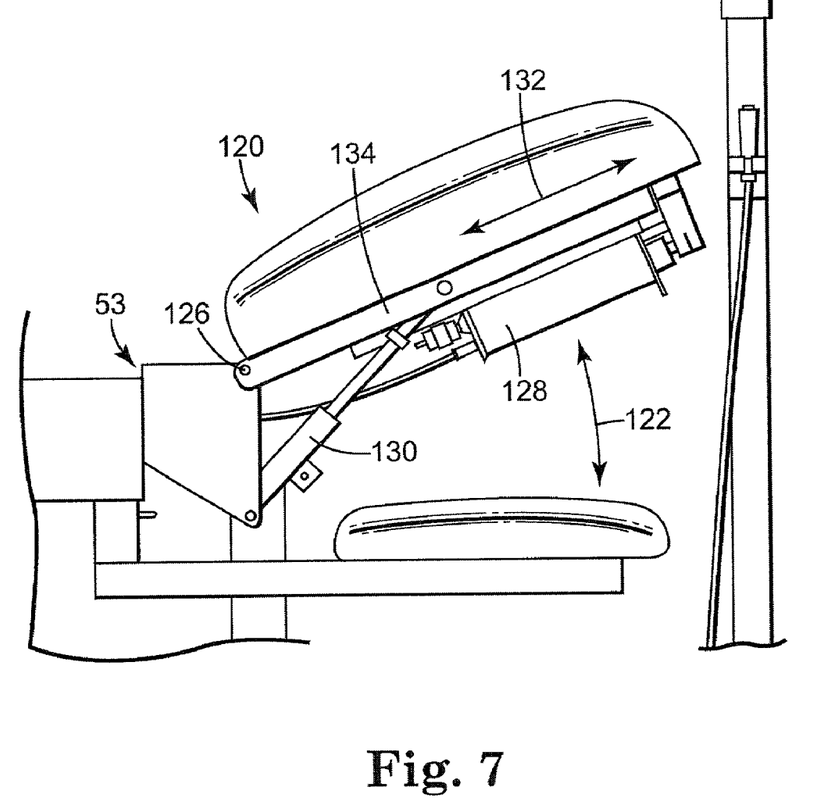
FIG. 7 illustrates a cervical assembly for use with a therapeutic apparatus in accordance with the present invention.

As illustrated in FIG. 7, an apparatus of the present invention may also provide a head supporting portion 120 for generally supporting the head of the patient. Head supporting portion 120 is slidingly attached to frame 134. The frame 134 is pivotally attached to platform portion 53 at pivot points 124, 126 (See FIG. 2), and is adapted to move along path 122. Preferably, the frame 134 is adapted to rotate at pivot points 124, 126 up to about 30 degrees from a horizontal plane. Locking mechanism 130 is provided for releasably retaining the frame 134 and head supporting portion 120 at various locations along path 122.

The head supporting portion 120 is adapted to move relative to frame 134 along an axis 132 under the power of actuator 128. Conventional ropes and pulleys are eliminated. Actuator 128 is preferably powered by the central source of compressed air 68 (see FIG. 2) to generate the cervical traction force. In the present therapeutic apparatus 10, the single power source 68 operates all of the actuators 56, 66, 128. Neck wedges 136 are preferably used to retain the patient's head to the head supporting portion 120 (see FIG. 2). The location of the neck wedges 136 is preferably adjust to accommodate patients of different sizes. Head strap 121 can optionally be used to retain the patient's head to the head supporting portion 120. A cervical traction assembly with adjustable neck wedges suitable for use in the present invention is disclosed in U.S. patent application Ser. No. 08/817,444, entitled Portable Traction Device and U.S. Pat. No. 6,171,273. The processor 70 preferably retains cervical traction protocols as well.

Figure 3:
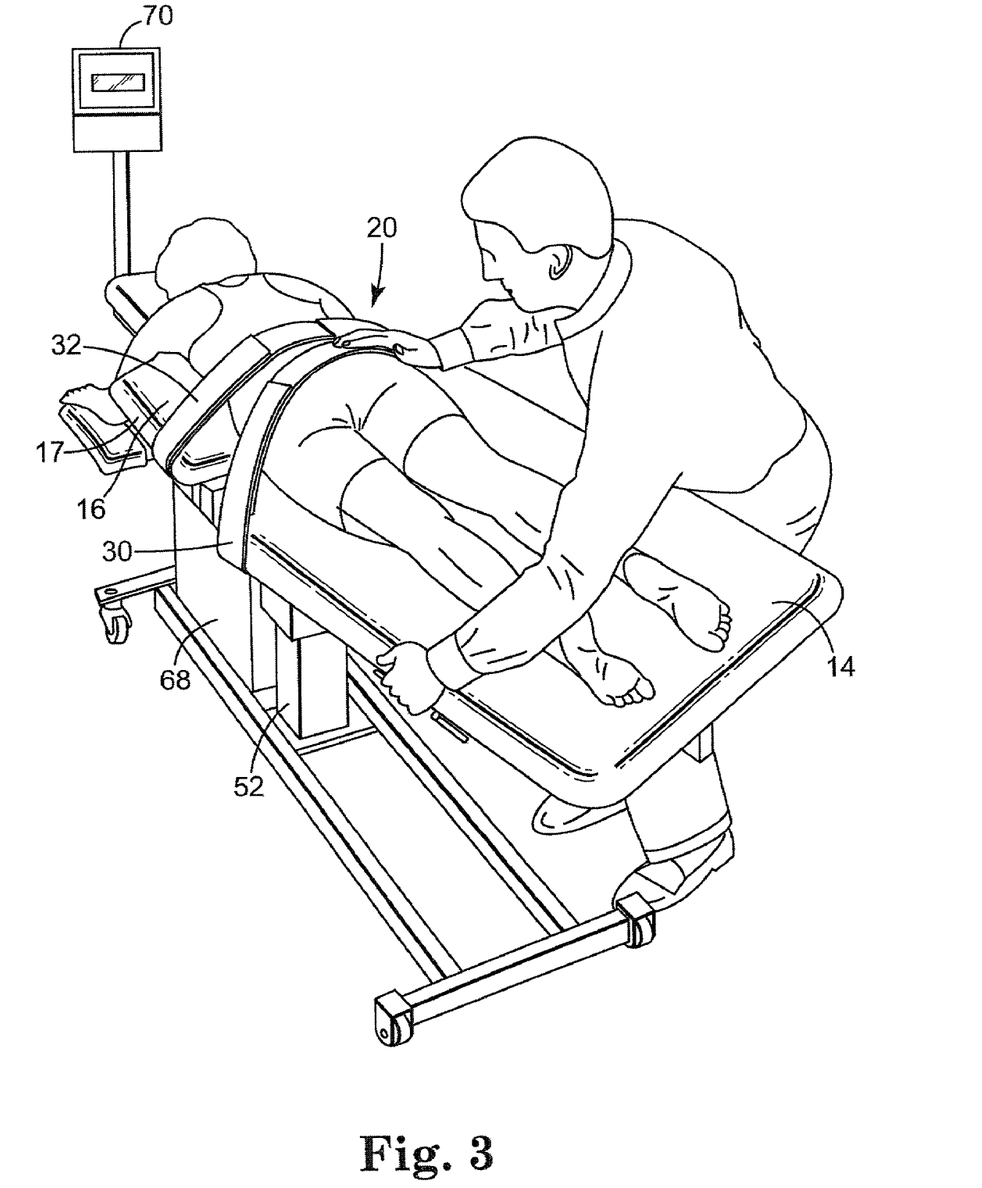
FIG. 3 illustrates a patient being treated with a therapeutic apparatus in accordance with the present invention.

The present invention also provides a method of treating a patient with the apparatus generally described above. FIG. 3 illustrates a patient being treated on an apparatus of the present invention. Support member 52 is adjusted to a height that easily facilitates a patient mounting the apparatus. First body supporting portion 14 is then moved along a path comprising at least one rotational degree of freedom to accommodate for any postural deformities of the patient. The patient is then placed and supported on the first and second body supporting portions 14, 16 in either a prone or supine position, and is secured to first body and second body supporting portions 14, 16 by securing system 20. In FIG. 3, securing system 20 comprises a first belt 30 connected to the support frame, near each side edge of first body supporting portion 14 and a second belt 32 is connected to second body supporting portion 16 in a similar manner. First belt 30 is tightened around the navel region of the patient, just above the iliac crests. Second belt 32 is tightened around the ribcage of the patient, just above the lumbar region. The belts may overlap slightly.

Next, first body supporting portion 14 is moved relative to second body supporting portion 16 along longitudinal axis 18 (see FIG. 1). As the distance between the first and second body supporting portion is increased, a traction force is applied to the patient's lumbar region by the first and second belts. Further, because the first body supporting portion 14 has been moved along a path comprising at least one rotational degree of freedom, the traction force is applied at an angle that compensates for a patient's postural deformities. As the distance between the first and second body supporting portions is decreased, the traction force applied to the patient's lumbar region is decreases.

Many variations of the above described method can be accomplished by an apparatus of the present invention. For example, to further treat a patient's postural deformities, first body supporting portion 14 can be moved along a path comprising at least one rotational degree of freedom after the patient is secured to the table and even during the application of traction force to the patient. Further, the table can be releasably retained anywhere along the path during treatment to accommodate the patient's condition. It may even be desirable to retain first body supporting portion 14 at multiple locations along a path during a treatment cycle. Additionally, the traction force created by first body supporting portion 14 moving away from second body supporting portion 16 along longitudinal axis 18 can be static (i.e. constant application of a force during a period of time) or intermittent (application of greater force for a period of time followed by a lesser force for a period of time). Further yet, the patient can be treated in either the supine or prone position and/or both, without adjusting the apparatus.

Prior to beginning therapy, a treatment protocol can be entered into processor 70 to facilitate some or all of the therapeutic steps. In a preferred embodiment, processor 70 provides a touch control screen to assist a health care professional in entering the treatment protocol. Data input such as the mode of lumbar treatment (e.g. static or intermittent), force ramp up time, force ramp down time, hold time, rest time, rest force, maximum force, and treatment time can all be entered to create a desired treatment protocol. The processor 70 communicates with the power source (in the illustrated embodiment the source of compressed air 68) to power the actuators 56, 66, 128 and to provide the designated movement between the first body supporting portion, second body supporting portions, and/or the head supporting portion 14, 16, 120.

Performance characteristics of the present invention include improved ability to treat patients with postural deformities, greater ease in the treatment of patients, and reduced set-up time. By providing an apparatus that is adapted to move along a path comprising at least one rotational degree of freedom, an apparatus of the present invention can treat patients with postural deformities who could not be adequately treated with conventional traction devices. Further, the securing system 20 provides a more efficient and less cumbersome mechanism of applying traction force to a patient. Further yet, a single or series of patients can be treated in either the prone or supine position or both, without adjusting or altering an apparatus of the present invention. Thus, the invention has improved performance characteristics, while also being easier and faster to use.

All of the patents and patent applications disclosed herein, including those set forth in the Background of the Invention, are hereby incorporated by reference. Although specific embodiments of this invention have been shown and described herein, it is to be understood that these embodiments are merely illustrative of the many possible specific arrangements that can be devised in application of the principles of the invention. Numerous and varied other arrangements can be devised in accordance with these principles by those of ordinary skill in the art without departing from the scope and spirit of the invention.

What is claimed is:

1. A therapeutic apparatus for a patient comprising:
   a support frame including a first body supporting portion and a second body supporting portion, the first body supporting portion moveable relative to the second body supporting portion along a longitudinal axis;
   a first actuator adapted to move the first body supporting portion relative to the second body supporting portion along the longitudinal axis;
   a securing system adapted to secure a patient to the first and second body supporting portions; and
   a linkage mechanism adapted to move the first body supporting portion along a path relative to the second body portion, the path comprising at least one rotational degree of freedom,
   wherein the first actuator is adapted to move the first body supporting portion along the longitudinal axis without interfering with movement of the first body supporting portion along the path comprising at least one rotational degree of freedom.

2. The therapeutic apparatus of claim 1 wherein the at least one rotational degree of freedom comprises two rotational degrees of freedom.

3. The therapeutic apparatus of claim 1 wherein the at least one rotational degree of freedom comprises three rotational degrees of freedom.

4. The therapeutic apparatus of claim 1 wherein the linkage mechanism is adapted to move the first body supporting portion along the path comprising at least one rotational degree of freedom simultaneously with movement of the first body supporting portion relative to the second body supporting portion along the longitudinal axis.

5. The therapeutic apparatus of claim 1 wherein the securing system comprises a first belt attachable to the first body supporting portion and adapted to secure the patient to the first body supporting portion and a second belt attachable to the second body supporting portion and adapted to secure the patient to the second body supporting portion.

6. The therapeutic apparatus of claim 1 wherein the first actuator comprises a pneumatic actuator.

7. The therapeutic apparatus of claim 1 wherein the first actuator comprises a double-acting pneumatic cylinder.

8. The therapeutic apparatus of claim 1 comprising a source of compressed air adapted to actuate the first actuator.

9. The therapeutic apparatus of claim 1 comprising a second actuator adapted to move the first body supporting portion along at least one rotational degree of freedom.

10. The therapeutic apparatus of claim 9 wherein the rotational degree of freedom comprises pitch movement.

11. The therapeutic apparatus of claim 1 comprising:
a second actuator adapted to displace a portion of the therapeutic apparatus; and
a single power source connected to the first and second actuators.

12. The therapeutic apparatus of claim 1 comprising:
a second actuator adapted to move a head supporting portion of a cervical traction device relative to the first body supporting portion; and
a single power source connected to the first and second actuators.

13. The therapeutic apparatus of claim 1 comprising:
a head supporting portion moveable relative to the second body supporting portion; and
a pair of neck wedges adapted to retain a patient's head to the head supporting portion.

14. The therapeutic apparatus of claim 1 comprising at least one locking mechanism adapted to releasably retain the first body supporting portion in a plurality of locations along the path relative to the second body supporting portion.

15. The therapeutic apparatus of claim 14 wherein the at least one locking mechanism is continuously adjustable.

16. The therapeutic apparatus of claim 14 comprising at least one locking mechanism for each rotational degree of freedom.

17. The therapeutic apparatus of claim 1 comprising a sliding mechanism supporting the first body supporting portion.

18. The therapeutic apparatus of claim 1 wherein the linking mechanism comprises a roll mechanism.

19. The therapeutic apparatus of claim 1 wherein the linking mechanism comprises a pitch mechanism.

20. The therapeutic apparatus of claim 1 wherein the linking mechanism comprises a yaw mechanism.

21. The therapeutic apparatus of claim 1 wherein the linking mechanism comprises a cantilever structure pivotally attached to the support frame.

22. The therapeutic apparatus of claim 1 wherein the support frame includes a first adjustable member adapted to adjust the height of the first and second body supporting portions.

23. The therapeutic apparatus of claim 1 comprising a cervical traction member.

24. The therapeutic apparatus of claim 1 comprising a processor adapted to communicate with the apparatus.

25. The therapeutic apparatus of claim 1 comprising a processor adapted to retain a plurality of traction protocols.

26. The therapeutic apparatus of claim 1 comprising a processor adapted to retain a plurality of cervical and lumbar traction protocols.

27. The therapeutic apparatus of claim 1 wherein the first actuator comprises one of a hydraulic actuator, a rack and pinion structure, a worm gear, or a solenoid.

28. The therapeutic apparatus of claim 1 comprising a traction device that isolates and concentrates a traction force on a specific area of the patient's body.

29. The therapeutic apparatus of claim 1 adapted to exert a therapeutic traction force on a patient's spine to relieve pressures.

30. The therapeutic apparatus of claim 1 capable of producing forces and positions required to cause decompression of intervertebral discs.

31. The therapeutic apparatus of claim 1 capable of producing unloading due to distraction and positioning.

32. The therapeutic apparatus of claim 1 capable of treating back pain, neck pain, herniated discs, protruding discs, degenerative disc disease, posterior facet syndrome and sciatica.

33. A method of treating back pain in a patient comprising the steps of:
providing a therapeutic apparatus having a support frame with a first body supporting portion, a second body supporting portion, and a first actuator adapted to move the first body supporting portion relative to the second body supporting portion along a longitudinal axis;
supporting the patient along the first body supporting portion and the second body supporting portion;
securing the patient to the apparatus with a securing system;
moving the first body supporting portion along a path relative to the second body supporting portion, the path comprising at least one rotational degree of freedom; and
activating the actuator to move the first body supporting portion relative to the second body supporting portion along the longitudinal axis to affect the distance between the first body supporting portion and the second body supporting portion without interfering with the step of moving the first body supporting portion along the path comprising at least one rotational degree of freedom.

34. The method of claim 33 wherein the step of moving the first body supporting portion along a path comprising at least one rotational degree of freedom occurs simultaneously with moving the first body supporting portion along the longitudinal axis.

35. The method of claim 33 wherein the step of moving the first body supporting portion along a path comprising at least one rotational degree of freedom occurs after the first body supporting portion is moved along the longitudinal axis.

36. The method of claim 33 wherein the step of moving the first body supporting portion along a path comprising at least one rotational degree of freedom occurs before the first body supporting portion is moved along the longitudinal axis.

37. The method of claim 33 comprising securing the patient to the first body supporting portion with a first belt and securing the patient to the second body supporting portion with a second belt.

38. The method of claim 33 comprising releasably retaining the first body supporting portion along one or more locations along the path relative to the second body supporting portion.

39. The method of claim 33 comprising supporting the patient along the first body supporting portion and second body supporting portion in a prone or supine position.

40. The method of claim 33 wherein the therapeutic apparatus includes a processor, the method comprising programming one or more treatment protocols into the processor.

41. The method of claim 33 wherein the therapeutic apparatus includes a processor, the method comprising storing one or more treatment protocols into the processor.

42. The method of claim 33 comprising securing the patient to at least one of the first body supporting portion and the second body supporting portion with a high friction surface.

43. The method of claim 33 comprising the step of isolating and concentrating a traction force on a specific area of the patient's body.

44. The method of claim 33 comprising the step of exerting a therapeutic traction force on a patient's spine to relieve pressure.

45. The method of claim 33 comprising the step of producing forces and positions required to cause decompression of intervertebral discs.

46. The method of claim 33 comprising the step of producing unloading due to distraction and positioning.

47. The method of claim 33 comprising the step of treating back pain, neck pain, herniated discs, protruding discs, degenerative disc disease, posterior facet syndrome and sciatica.

48. A therapeutic apparatus for a patient comprising:
    a support frame including a first body supporting portion and a second body supporting portion, the first body supporting portion moveable relative to the second body supporting portion along a longitudinal axis;
    a linking mechanism pivotally securing the first body supporting portion relative to the second body portion such that the first body supporting portion is adapted to move along a path relative to the second body supporting portion, the path comprising at least one rotational degree of freedom comprising pitch movement;
    a first actuator adapted to move the first body supporting portion relative to the second body supporting portion along the longitudinal axis;
    a second actuator adapted to move the first body supporting portion relative to the second body supporting portion along the at least one rotational degree of freedom comprising pitch movement; and
    a securing system adapted to secure the patient to the first and second body supporting portions.

49. The apparatus of claim 48 wherein the linking mechanism is adapted to provide pitch movement of the first body portion above a neutral position and below the neutral position.

50. The apparatus of claim 48 further comprising a processor adapted to move the actuator provide automated pitch movement in response to a programmed pitch value.

51. The therapeutic apparatus of claim 48 wherein the securing system comprises high friction surface on at least one of the first body supporting portion and the second body supporting portion.

52. A therapeutic apparatus for a patient comprising:
    a support frame including a first body supporting portion and a second body supporting portion, the first body supporting portion moveable relative to the second body supporting portion along a longitudinal axis;
    a first actuator adapted to move the first body supporting portion relative to the second body supporting portion along the longitudinal axis;
    a securing system adapted to secure a patient to the first and second body supporting portions;
    a linking mechanism adapted to move the first body supporting portion along a path relative to the second body supporting portion, the path comprising at least one rotational degree of freedom; and
    a processor adapted to store at least one pre-programmed traction protocol; wherein the first actuator is adapted to move the first body supporting portion along the longitudinal axis without interfering with movement of the first body supporting portion along the path comprising at least one rotational degree of freedom.

53. The therapeutic apparatus of claim 1 wherein the securing system comprises high friction surface on at least one of the first body supporting portion and the second body supporting portion.

54. The therapeutic apparatus of claim 52 wherein the securing system comprises high friction surface on at least one of the first body supporting portion and the second body supporting portion.

55. A spinal decompression apparatus comprising:
    a support frame including a first body supporting portion and a second body supporting portion, the first body supporting portion moveable relative to the second body supporting portion along a longitudinal axis;
    a first actuator adapted to move the first body supporting portion relative to the second body supporting portion along the longitudinal axis to provide spinal decompression;
    a securing system adapted to secure a patient to the first and second body supporting portions; and
    a linkage mechanism adapted to move the first body supporting portion along a path relative to the second body portion, the path comprising at least one rotational degree of freedom,
    wherein the first actuator is adapted to move the first body supporting portion along the longitudinal axis without interfering with movement of the first body supporting portion along the path comprising at least one rotational degree of freedom.

56. A method of performing spinal decompression on a patient comprising the steps of:
    providing a therapeutic apparatus having a support frame with a first body supporting portion, a second body supporting portion, and a first actuator adapted to move the first body supporting portion relative to the second body supporting portion along a longitudinal axis;
    supporting the patient along the first body supporting portion and the second body supporting portion;
    securing the patient to the apparatus with a securing system;
    moving the first body supporting portion along a path relative to the second body supporting portion, the path comprising at least one rotational degree of freedom; and activating the actuator to move the first body supporting portion relative to the second body supporting portion along the longitudinal axis to affect the distance between the first body supporting portion and the second body supporting portion to provide spinal decompression, without interfering with the step of moving the first body supporting portion along the path comprising at least one rotational degree of freedom.

57. A therapeutic apparatus for a patient comprising:
a support frame including a first body supporting portion and a second body supporting portion, the first body supporting portion moveable relative to the second body supporting portion along a longitudinal axis;
first means for moving the first body supporting portion relative to the second body supporting portion along the longitudinal axis;
securing means for securing a patient to the first and second body supporting portions; and
linking means for moving the first body supporting portion along a path relative to the second body portion, the path comprising at least one rotational degree of freedom, wherein the first means is adapted to move the first body supporting portion along the longitudinal axis without interfering with movement of the first body supporting portion along the path comprising at least one rotational degree of freedom.

58. A therapeutic apparatus for a patient comprising:
a support frame including a first body supporting portion and a second body supporting portion, the first body supporting portion moveable relative to the second body supporting portion along a longitudinal axis;
first means adapted to move the first body supporting portion relative to the second body supporting portion along the longitudinal axis;
securing means adapted to secure a patient to the first and second body supporting portions;
linking means adapted to move the first body supporting portion along a path relative to the second body supporting portion, the path comprising at least one rotational degree of freedom; and
processor means adapted store at least one pre-programmed traction protocol.

* * * * *